United States Patent
Paulczynski et al.

(10) Patent No.: US 6,482,971 B2
(45) Date of Patent: Nov. 19, 2002

(54) PROCESS FOR THE PREPARATION OF 3-ALKOXYACRYLONITRILE

(75) Inventors: Renate Paulczynski, Herne (DE); Manfred Kaufhold, Marl (DE); Artur Hunds, Bonn (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/921,891

(22) Filed: Aug. 6, 2001

(65) Prior Publication Data

US 2002/0028962 A1 Mar. 7, 2002

(30) Foreign Application Priority Data

Aug. 5, 2000 (DE) ......................................... 100 38 369

(51) Int. Cl.$^7$ ........................................... C07C 255/00
(52) U.S. Cl. ....................................................... 558/435
(58) Field of Search ......................................... 558/435

(56) References Cited

U.S. PATENT DOCUMENTS

| 5,026,852 A | 6/1991 | Von Itter et al. |
| 5,767,325 A | 6/1998 | Schroeder et al. |

FOREIGN PATENT DOCUMENTS

| DE | 3434142 A1 | 3/1986 |
| DE | 4433949 A1 | 3/1996 |
| EP | 0 028 316 A1 | 5/1981 |
| JP | 58-26855 | 2/1983 |

OTHER PUBLICATIONS

S. M. McElvain et al, "The Preparation, Alcoholysis and Reduction of Cyanoacetaldehyde Diethylacetal Malonaldehyde Tetraethylacetal", Bull. soc. chim., 8, 128, 1941, pp. 2657–2660.
Abstract, JP 60116674, Jun. 24, 1985.
Abstract, JP 60120869, Jun. 28, 1985.
Abstract, JP 11092460, Apr. 6, 1999.
Abstract, JP 1156963, Jun. 20, 1989.

*Primary Examiner*—T. A. Solola
*Assistant Examiner*—Joseph Murray
(74) *Attorney, Agent, or Firm*—Oblon, Spivak, McClelland, Maier & Neustadt, P.C.

(57) ABSTRACT

The present invention provides a process, which includes:
  preparing 3-alkoxyacrylonitrile from 3,3-dialkoxypropionitrile by catalytically eliminating alcohol from 3,3-dialkoxypropionitrile in the presence of at least one aromatic sulfonic acid catalyst and at least one high-boiling solvent. Another embodiment of the invention provides a method of producing a pharmaceutical compound, which includes the above-described process. Another embodiment of the invention provides a method of producing a cosmetic product, which includes the above-described process.

18 Claims, No Drawings

PROCESS FOR THE PREPARATION OF 3-ALKOXYACRYLONITRILE

BACKGROUND OF THE INVENTION

1. Field of the Invention

The invention relates to a process for the preparation of 3-alkoxyacrylonitrile by elimination of an alcohol from 3,3-dialkoxypropionitrile in accordance with the scheme:

$$NC-CH_2-CH(OR)_2 \rightarrow NC-CH=CH-OR+ROH$$

wherein R may be an alkyl group.

2. Discussion of the Background

3-Alkoxyacrylonitriles are important intermediates for the preparation of pharmaceutical and cosmetic products. Syntheses of 3-alkoxyacrylonitriles by alcohol elimination from the corresponding acetals are known from the literature. For example, in J. Amer. Soc. 69, 2657, McElvain, Clarke describes this cleavage using concentrated sulfuric acid as catalyst. However, the yield mentioned therein of a process which is evidently not optimized is much too low for industrial implementation. Furthermore, the handling of concentrated sulfuric acid is a disadvantage.

JP 58026855 and EP 0 776 879 propose gas-phase processes using solid catalysts, which do give good yields, but can only be realized industrially in a relatively elaborate manner because they need special reactors and require valuable catalysts which, following use, have to be disposed of by a relatively complex procedure.

Thus there remains a need for a process which is easy to realize industrially, which can be carried out in customary stirred reactors, particularly in the case of a discontinuous procedure, and which produces high yields.

SUMMARY OF THE INVENTION

Accordingly, one object of the invention is to provide a process which is easy to realize industrially.

Another object of the present invention is to provide a process that can be carried out in customary stirred reactors, and particularly in the case of a discontinuous procedure.

Another object of the present invention is to provide a process that produces high yields.

These and other objects may be accomplished with the present invention, the first embodiment of which provides a process, which includes:

preparing 3-alkoxyacrylonitrile from 3,3-dialkoxypropionitrile by catalytically eliminating alcohol from 3,3-dialkoxypropionitrile in the presence of at least one aromatic sulfonic acid catalyst and at least one high-boiling solvent.

Another embodiment of the invention provides a method of producing a pharmaceutical compound, which includes the above-described process.

Another embodiment of the invention provides a method of producing a cosmetic product, which includes the above-described process.

DESCRIPTION OF THE PREFERRED EMBODIMENTS

Various other objects, features and attendant advantages of the present invention will be more fully appreciated as the same becomes better understood from the following detailed description of the preferred embodiments of the invention.

The invention preferably provides a process in which an aromatic sulfonic acid in combination with a high-boiling solvent as catalyst is used for the alcohol elimination.

More preferably, the invention provides a process for the preparation of 3-alkoxyacrylonitrile by catalytic elimination of an alcohol from 3,3-dialkoxy-propionitrile in the presence of an aromatic sulfonic acid in combination with a high-boiling solvent as catalyst, where the alkyl group of the alcohol is unbranched or branched and contains 1 to 6, preferably 1 to 4, carbon atoms. Most preferably, the alkyl group is the methyl, ethyl, n-propyl, isopropyl, n-butyl or isobutyl group.

Surprisingly, it has been found that the use of these strong acids leads to high yields, preferably to yields greater than 98%, more preferably greater than 98.5%, and more particularly preferably greater than 99%, based on the use of acetal, and very pure products are produced directly during the reaction.

Preferably, the process for the preparation of 3-alkoxyacrylonitrile by elimination of an alcohol from 3,3-dialkoxypropionitrile is in accordance with the scheme:

$$NC-CH_2-CH(OR)_2 \rightarrow NC-CH=CH-OR+ROH$$

wherein R may be an unbranched or branched alkyl group having 1 to 6, preferably 1 to 4, carbon atoms.

The positive effect of the strong sulfonic acids during the acetal cleavage in accordance with the present invention is entirely surprising since German Patent Application DE 44 33 949 teaches expressly that weak acids, such as, in particular, 2,2-disubstituted carboxylic acids, as catalysts in the cleavage of acetals produce considerably better yields than aromatic and alkylaromatic sulfonic acids. On the contrary, it has been found that these branched acids are entirely unsuitable for the cleavage of the acetals of propionitrile.

During the preparation of the 3-alkoxyacrylonitriles from the corresponding acetals, the following process steps are preferably carried out:

1. The acetal (3,3-dialkoxypropionitrile) is heated together with the aromatic sulfonic acid and a high-boiling solvent, and the alkanol is distilled off at atmospheric pressure or under a slight vacuum.
2. Where appropriate, the temperature is then lowered, the pressure is reduced and the 3-alkoxyacrylonitrile is distilled off.
3. The liquid and pumpable residue is used directly for further cleavages without work-up. Any bleeding-off which becomes necessary is minimal.

The process offers economical and ecological advantages because it does not require special apparatuses and costly chemicals (catalysts) and does not produce products which have to be disposed of in a complex manner.

Preferable catalysts for the alkanol elimination (see point 1) include aromatic sulfonic acids having 1 to 3 sulfonic acid groups, in particular monosulfonic acids, such as benzenesulfonic acid, p-toluene sulfonic acid, naphthalene sulfonic acid and, particularly preferably alkyl benzenesulfonic acids, advantageously those having unbranched or branched $C_{10}$- to $C_{13}$-alkyl radicals. Combinations are possible. The catalysts are preferably used in amounts from 0.2 to 15% by weight, preferably from 1 to 10% by weight, particularly preferably from 2 to 4% by weight, based on acetal used. These ranges include all values and subranges therebetween, including 0.3, 0.5, 0.9, 3, 6, 8, 9, 11, 12, 13 and 14.

Preferred solvents include high-boiling solvents which are inert under the reaction conditions. That applies in particular to high-boiling hydrocarbons, such as mineral oils and paraffins having, for example, 20–30 carbon atoms and, for example, boiling points above 250° C., alicyclics and polyalicyclics, such as, for example, decalin and tetralin, alkylaromatics and polyaromatics, such as, for example, $C_{10}$–$C_{13}$-alkylbenzenes, ethers, such as, for example, di-n-decyl ether and di-n-lauryl ether, and chlorinated hydrocarbons, such as, for example, 1,10-dichlorodecane and 1,12-dichlorododecane. Combinations are possible. For cost reasons, preference is given to using low-cost technical-grade mixtures, such as, for example, heat-transfer oils. Preferred examples thereof include dibenzyltoluenes. Preferably, the boiling point of the solvent is above 250° C., more preferably above 275° C. and most preferably above 290° C. These ranges include all values and subranges therebetween, including 255, 260, 270, 280, 300, 310 and 320° C.

The solvent is preferably used in amounts of from 0.5 to 20% by weight, more preferably from 1 to 10% by weight, and particularly preferably from 2 to 8% by weight, based on acetal used. These ranges include all values and subranges therebetween, including 0.7, 0.9, 3, 4, 5, 6, 7, 9, 12, 14, 16, 18 and 19% by weight.

In the first stage, the eliminated alcohol is preferably distilled off and thus recovered as a product of value. Virtually complete conversion is achieved. The temperatures are preferably 100 to 200° C., more preferably 120 to 180° C. These ranges include all values and subranges therebetween, including 105, 110, 130, 140, 160, and 190° C. In order to accelerate the distillation, a pressure slightly below a atmospheric is preferred. More preferably, the pressure is 0.5 to less than 1 atm, more particularly preferably 0.6 to 0.9 atm, and most preferably 0.7 to 0.8 atm. These ranges include all values and subranges therebetween, including 0.55, 0.65, 0.75, 0.85 and 0.95 atm.

Preferably, the second process stage, removal by distillation of the 3-alkoxyacrylonitrile, is carried out under a reduced pressure of from about 1 to 200 hPa, more preferably 2 to 180, and more particularly preferably 3 to 160 hPa. These ranges include all values and subranges therebetween, including 5, 10, 20, 40, 80, 120, 170 and 190 hPa. Preferably, the removal and purification distillations of the target product occur simultaneously. The still temperatures during distillation are preferably 50 to 200° C., more preferably 80 to 180° C., and most preferably 100 to 160° C. These ranges include all values and subranges therebetween, including 75, 95, 125, 140, 155, 175 and 190° C.

The residue produced is homogeneous, of low viscosity and readily pumpable, i.e. is easy to handle on an industrial scale. It can be returned to the reaction without further treatment, thus saving catalyst and solvent. Virtually complete recycling is possible. Only the decomposition losses, which are scarcely avoidable and insignificant in terms of balance and cost, have to be compensated for.

The reaction can be carried out discontinuously or continuously, for example in two stirred apparatuses with a column.

3-alkoxyacrylonitrile are valuable building blocks in the synthesis of the pyrimidine base cytosine. For example, the reaction of 3-alkoxyacrylonitrile with urea and alcoholate to produce these important building blocks of nucleic acids is described in JP 11 092 460, DE 39 06 855 (corresponds to U.S. Pat. No. 5,026,852), and DE 34 34 142, the entire contents of each of which being hereby incorporated by reference. Cytosine is used in the pharmaceutical sector, for the synthesis of cytostatics, and urostatics, among other things.

So-called 5-aminopyrazoles and 5-aminooxazoles are also used in the pharmaceutical sector, as building blocks for synthesis. These compounds can also be produced by reacting alkoxyacrylonitriles with alkyl hydrazine or hydroxylamine. Examples for these types of synthesis are described in JP 1156963, JP 60120869, and JP 60116674, the entire contents of each of which being hereby incorporated by reference.

2,4-diaminopyrimidines are also accessible by reacting alkoxyacrylonitriles with guanidine (DE 29 44 145, the entire contents of which are hereby incorporated by reference).

EXAMPLES

Having generally described this invention, a further understanding can be obtained by reference to certain specific examples which are provided herein for purposes of illustration only and are not intended to be limiting unless otherwise specified.

Example

A glass apparatus was used which consisted of a 500 ml three-necked flask fitted with stirrer, a thermometer and a 20 cm-long distillation column with reflux divider and receivers.

308.2 g (2.04 mol) of 3,3-diethoxypropionitrile (94.9% pure)

30.0 g of dibenzyltoluene (Marlotherm)

8.0 g of $C_{10}$–$C_{13}$-n-alkyl benzenesulfonic acid (Marlon AS 3 acid) were used.

The three components were combined, a pressure of 600 hPa was produced and the mixture was heated. The elimination and distillation of the ethanol started from 120° C. The temperature was increased to 180° C. and ethanol was distilled off without residue. The temperature was then reduced to 90° C. and the pressure lowered to 20 hPa. At a reflux: take-off ratio of 2:1 and head temperatures of 83–92° C., 198.3 g of pale yellow 3-ethoxyacrylonitrile with a purity of 98.7% were produced. The residue which remained was 46.7 g. It was liquid at room temperature, homogeneous and readily soluble in methanol. The yield of 3-ethoxyacrylonitrile was 98.80, based on acetal used.

Comparative Example

The apparatus described above in the example was used.

308.2 g (2.04 mol) of 3,3-diethoxypropionitrile (94.9% pure);

25.0 g of dibenzyltoluene; and 1.0 g of concentrated sulfuric acid were used.

The procedure adopted was as described in the above example. 168.7 g of intensely yellow-colored 3-ethoxyacrylonitrile with a purity of 98.1% were produced as the main fraction. The yield is calculated as 83.5, based on acetal used.

The residue was black and of high-viscosity and contained black lumps. It was only partially soluble in methanol.

Obviously, numerous modifications and variations of the present invention are possible in light of the above teachings. It is therefore to be understood that within the scope of the appended claims, the invention may be practiced otherwise than as specifically described herein.

This application is based on patent application No. 100 38 369.6, filed Aug. 5, 2000, the entire contents of which are hereby incorporated by reference, the same as if set forth at length.

What is claimed is:

1. A process, comprising:
   preparing 3-alkoxyacrylonitrile from 3,3-dialkoxypropionitrile by catalytically eliminating alcohol from 3,3-dialkoxypropionitrile in the presence of at least one aromatic sulfonic acid catalyst and at least one high-boiling solvent.

2. The process as claimed in claim 1, wherein said alcohol is a branched or unbranched $C_{1-6}$ alcohol.

3. The process as claimed in claim 1, wherein the aromatic sulfonic acid catalyst has 1 to 3 sulfonic acid groups.

4. The process as claimed in claim 1, wherein the aromatic sulfonic acid catalyst is selected from the group consisting of benzenesulfonic acid, naphthalene sulfonic acid, p-toluene sulfonic acid, $C_{10}$–$C_{13}$-alkyl-benzenesulfonic acid, and combinations thereof.

5. The process as claimed in claim 1, wherein the aromatic sulfonic acid catalyst is selected from the group consisting of benzenesulfonic acid, p-toluene sulfonic acid, $C_{10}$–$C_{13}$-alkyl-benzenesulfonic acid, and combinations thereof.

6. The process as claimed in claim 1, wherein the aromatic sulfonic acid catalyst is present in an amount ranging from 0.2 to 15% by weight, based on the weight of the 3,3-dialkoxypropionitrile.

7. The process as claimed in claim 1, wherein said high-boiling solvent has a boiling point above 250° C. at atmospheric pressure.

8. The process as claimed in claim 1, wherein said high-boiling solvent is selected from the group consisting of mineral oil, paraffin, alicyclic solvent, polyalicyclic solvent, decalin, tetralin, alkylaromatic solvent, polyaromatic solvent, $C_{10}$–$C_{13}$-alkylbenzene, dibenzyltoluene, ether, di-n-decyl ether, di-n-lauryl ether, chlorinated hydrocarbon, 1,10-dichlorodecane, 1,12-dichlorododecane, and combinations thereof.

9. The process as claimed in claim 1, wherein said high-boiling solvent is selected from the group consisting of paraffin, mineral oil, alkylaromatic, ether, chlorinated hydrocarbon, and mixtures thereof.

10. The process as claimed in claim 1, wherein said high-boiling solvent is present in an amount ranging from 0.5 to 20% by weight, based on the weight of the 3,3-dialkoxypropionitrile.

11. The process as claimed in claim 1, wherein the catalytic elimination is carried out at a temperature ranging from 100 to 200° C.

12. The process as claimed in claim 1, further comprising removing said alcohol by distillation.

13. The process as claimed in claim 1, wherein the catalytic elimination is carried out at a pressure below atmospheric pressure.

14. The process as claimed in claim 1, further comprising removing said 3-alkoxyacrylonitrile by distillation.

15. The process as claimed in claim 1, further comprising removing said 3-alkoxyacrylonitrile by distillation under a reduced pressure ranging from about 1 to 200 hPa.

16. The process as claimed in claim 1, further comprising removing said 3-alkoxyacrylonitrile by distillation at a still temperature ranging from 50 to 200° C.

17. The process as claimed in claim 1, further comprising recycling the high-boiling solvent and the aromatic sulfonic acid catalyst to the process.

18. The process as claimed in claim 1, which is carried out discontinuously or continuously.

* * * * *